United States Patent [19]
Hendrix et al.

[11] Patent Number: 5,668,277
[45] Date of Patent: Sep. 16, 1997

[54] DEPOLYMERIZATION OF POLYAMIDES

[75] Inventors: Jan A. J. Hendrix, Obbicht; Martin Booij, Munstergeleen; Yvonne H. Frentzen, Venlo, all of Netherlands

[73] Assignee: DSM N.V., Netherlands

[21] Appl. No.: 632,082

[22] Filed: Apr. 15, 1996

[30] Foreign Application Priority Data

Apr. 14, 1995 [BE] Belgium ................ 09500347

[51] Int. Cl.$^6$ .................................. C07D 201/12
[52] U.S. Cl. ................ 540/540; 560/155; 564/198; 558/452
[58] Field of Search ............................... 540/540

[56] References Cited

U.S. PATENT DOCUMENTS

| | | | |
|---|---|---|---|
| 5,302,756 | 4/1994 | McKinney | 540/540 |
| 5,395,974 | 3/1995 | McKinney | 540/540 |

FOREIGN PATENT DOCUMENTS

| | | |
|---|---|---|
| 46-31541 | 9/1971 | Japan . |
| 54-084 525 | 7/1979 | Japan . |

*Primary Examiner*—Robert T. Bond
*Attorney, Agent, or Firm*—Cushman Darby & Cushman IP Group of Pillsbury Madison & Sutro, LLP

[57] ABSTRACT

One or more polyamides can be depolymerized in the presence of at least one nitrogen-containing compound. The depolymerization takes place at a pressure between about 0.5 and about 5 atm. The polyamide may be in the form of carpet waste or other heterogeneous form. Advantages include better selectivity towards the polyamide monomeric components and use of low pressure equipment to effect depolymerization.

20 Claims, No Drawings

DEPOLYMERIZATION OF POLYAMIDES

FIELD OF THE INVENTION

The invention relates to a process for the depolymerization of at least one polyamide, and in particular, depolymerization carried out in the presence of a nitrogen-containing compound at pressures between about 0.5 atmospheres and about 5 atmospheres.

DESCRIPTION OF RELATED ART

Polyamides such as the polyamide of production waste have been recycled for about 40 years. In general, recycling takes place at a polyamide producer or a polyamide fiber spinner. In recent years, recycling has increasingly been taking place at carpet manufacturers as well.

Polyamide depolymerization processes are generally relevant to recycling concepts for polyamide products, and in particular, for polyamide-containing carpets. In the future, it will become increasingly important to recycle waste carpet in an economical manner. Carpet waste generally includes both industrial carpet waste and so-called post-consumer carpet waste. At present, landfill capacity is nearing maximum utilization. Of course, the commercial feasibility of carpet waste recycling is dependent on the economics of the process. Also crucial is the technical capability of converting the polyamide in carpet waste to monomeric components which can be reused. Preferably, monomeric component reuse is immediately possible so that further conversion reactions of the monomeric components are unnecessary. Therefore, a need exists for further improvements in carpet waste recycling processes.

U.S. Pat. No. 5,302,756 discloses a polyamide depolymerization process. Depolymerization of nylon 6,6 or a mixture of nylon 6 and nylon 6,6 is disclosed which is carried out in the presence of ammonia to yield monomeric components. Phosphate catalyst may also be present. A drawback, however, is the relatively low selectivity towards the polyamide monomeric components. For nylon 6, the monomeric components are caprolactam and caprolactam precursors. Caprolactam precursors are compounds such as aminocaproic acid which can be used directly for the preparation of polyamide without first being converted to some related compound.

An additional disadvantage disclosed in U.S. Pat. No. 5,302,756 is the relatively high depolymerization pressure. The pressure is at least 100 psig, or about 7 atmospheres, and in fact, Table 3 of this patent discloses that increasing pressure increases the overall yield to monomeric products. There is no indication that low pressure depolymerization would be possible or would result in the high selectivities achieved by the present invention.

JP 46-31541 discloses a high pressure autoclave process in which polyamide is depolymerized in the presence of water or aqueous ammonia. A relatively low pressure process is not disclosed which could be effected outside of an autoclave. The pressures disclosed in the examples of JP46-31541 are estimated to be about 80 and up to about 200 bars.

JP-54-84525 discloses a process for preparing aminocapronitriles by treatment of lactams and continuously taking the product in the gaseous phase out of the system. Aminocapronitriles, however, are not desired monomeric components which are isolated in high selectivity in the present invention. The reaction pressure is disclosed as depending on the reaction temperature, but in general, reaction pressure is disclosed as ranging from normal pressure to about 100 kg/cm$^2$.

SUMMARY OF THE INVENTION

An object of the present invention is to provide a process that yields a better selectivity towards the monomeric components of polyamides.

An additional object is to provide a relatively low pressure depolymerization process.

An additional object is to provide a continuous depolymerization process.

These and other objects can be achieved in a process comprising the step of heating at least one polyamide comprising nylon 6 in the presence of ammonia, an amine, or a mixture thereof at a temperature between about 200° C. and about 400° C. and at a pressure between about 0.5 atm and about 5 atm to effect at least partial depolymerization of the polyamide and yield monomeric components of the polyamide.

Advantages of this process include higher selectivity to monomeric products. In contrast, JP-54-84525 discloses a process wherein large amounts of undesired aminocapronitrile are produced which reduces selectivity.

An additional advantage is that investment costs for a high-pressure depolymerization facility are prevented which makes the process very economically attractive. In U.S. Pat. No. 5,302,756, by contrast, the depolymerization is carried out at pressures of at least 7 atm. In particular, its examples disclose pressures varying from 30 to 300 atm, and illustrate that higher pressures are preferred because the higher the pressure, the higher the overall yield.

DETAILED DESCRIPTION OF THE PRESENT INVENTION

In general, the polyamide which can be depolymerized with good selectivity can be, for example, nylon 6 or mixtures of nylons. As disclosed further herein, the polyamide may be in relatively pure form or in the relatively impure form of a mixture of polyamide and non-polyamide components. Selectivities greater than about 60%, and preferably, greater than about 80%, can be achieved by the present invention.

Monomeric components from nylon 6 include caprolactam and aminocaproic acid and are distinguished from by-products like aminocaproamide and aminocapronitrile which are not desired monomeric components in the present invention. Aminocaproic acid is a precursor to caprolactam.

In the present process, depolymerization of polyamide is preferred. Depolymerization takes place at a pressure between about 0.5 and about 5 atmospheres, and preferably, between about 0.9 and about 3 atmospheres.

The nitrogen-containing compound present during polyamide depolymerization is not particularly limited, but in general, will be a Lewis base type of nitrogen-containing compound, or a mixture thereof.

Preferably, the nitrogen-containing compound is ammonia, an amine, or a mixture thereof. The ammonia can be in the form of pure ammonia or aqueous ammonia. The amine can be a primary, secondary, or tertiary amine, or a monoamine, diamine, or polyamine. In general, the amine can be substituted with alkyl, cycloalkyl, and aromatic groups, or mixtures of these groups without particular limitations.

More preferably, the amine is at least one of the following: (i) an amine containing a $C_1$–$C_{20}$ aliphatic or cycloaliphatic group, (ii) a diamine containing a $C_1$–$C_{20}$ aliphatic or cycloaliphatic group, (iii) a polyamine containing a $C_1$–$C_{20}$ aliphatic or cycloaliphatic group, (iv) a $C_6$–$C_{20}$ aromatic amine, (v) a $C_6$–$C_{20}$ aromatic diamine, or (vi) a $C_6$–$C_{20}$ aromatic polyamine.

Examples of alkyl and cycloalkyl amines include dimethylamine, diethylamine, dipropylamine, triethylamine, tripropylamine, aminomethane, aminoethane, aminopropane, aminobutane, aminopentane, aminohexane, aminododecane, 1,2-diaminoethane, 1,3-diaminopropane, diaminobutane (DAB), 1,4-diaminohexane (HDA), 1,5-diaminohexane (DAH), 1,6-diaminohexane (HMDA), dicyclohexylamine, diaminocyclohexane, 4-aminomethyl-1,8-diaminooctane, 3-aminomethyl-1,6-diaminohexane, bis-ethylene triamine, bistetramethylene triamine, and bishexamethylene triamine. The alkyl amine can be an amino (alkyl)-substituted piperidine compound, or an amino(alkyl)-substituted aromatic compound. The site of amino group substitution is not critical.

Examples of aromatic amines include aniline, diphenylamine, N-methylaniline, N,N-dimethylaniline, p-toluidine, 1-amino-2-phenylethane and substituted derivatives thereof.

Preferably, a nitrogen-containing compound is used that has a boiling point below the boiling point of caprolactam, which is about 270° C. at atmospheric pressure, or about 139° C. at 12 mm Hg. In particular, $NH_3$, aminoethane, aminopropane, diaminoethane, diaminopropane, diaminobutane or diaminohexane are preferred nitrogen-containing compounds. Mixtures of amines, with or without ammonia, are also contemplated.

The amount of nitrogen-containing compound is generally at least about 1 mole, and preferably more than about 2 moles, per mole of amide group in the polyamide to be depolymerized. In general, the amount of nitrogen-containing compound will be less than about 250 moles, and preferably less than about 100 moles, of nitrogen-containing compound per mole of amide group.

In addition to the nitrogen-containing compound, at least one additional component may be present during depolymerization which accelerates the reaction rate, improves selectivity, or both. This component can be termed an accelerator which encompasses both accelerators and catalysts. The accelerator can be in the form of a compound, salt, or oxide particle, and is preferably at least one of (i) a Lewis acid, (ii) a Bronsted acid, or (iii) nylon 6 oligomer or oligomers, wherein oligomer means the molecular weight is less than about 1,500.

Lewis acids can be oxide particles such as, for example, $Al_2O_3$ and $SiO_2$. Additional examples include rare earth metal oxides such as, for example, lanthanum and cerium oxides. Brønsted acids can be, for example, $H_3PO_4$, $H_3BO_3$, or salts thereof, including ammonium salts such as ammonium dihydrogen phosphate. Acids that do not lead to tar formation during depolymerization are generally contemplated. Accelerators are disclosed in U.S. Pat. No. 5,302,756, the complete disclosure of which is hereby incorporated by reference.

In general, the accelerator is present in an amount of about 0.1 to about 20 wt. % relative to the nitrogen-containing compound, and preferably, between about 1 and about 10 wt. %. After depolymerization, the catalyst or reaction accelerator can be in some cases advantageously recycled for further depolymerization reactions.

It is also possible to accelerate the reaction and improve selectivity with use of metallic components including metallic compounds and salts which are capable of complexing with the ammonia or amine. The metallic component can be, for example, based on a group VIII or group IB transition metal such as, for example, copper or cobalt. Examples of the metallic component include copper and cobalt compounds or salts such as copper halides or sulfides and cobalt halides or sulfides. The valency of the metal is not critical, and the halogen can be, for example, bromide or chloride. In this case, the metallic component is present in amount of about 0.1 to about 10 wt. % relative to the nitrogen-containing compound, and preferably, between about 0.5 to about 5 wt. %. Still other suitable metallic compounds are disclosed in U.S. Pat. No. 5,395,974, the complete disclosure of which is hereby incorporated by reference.

Depolymerization can also be carried out in the presence of water. The amount of water is in general at most about 50 wt. %, and preferably at most about 20 wt. %, and more preferably at most about 10 wt. % relative to the polyamide. The polyamide usually contains some water, and the process is generally carried out in the presence of more than 1 wt. % water. Although JP-46-31,541 discloses the depolymerization of polyamides in the presence of ammonia and water, the depolymerization is carried out at high pressures in an autoclave.

In the present invention, the effective depolymerization temperature can be, for example, between about 200° C. and about 400° C. Preferably, the temperature is between about 250° C. and about 350° C.

Depolymerization can be carried out by contacting the nitrogen-containing compound with the polyamide in molten form. The polyamide reacts to yield monomeric components and by-products, which are preferably removed together with the nitrogen-containing compound via the gas phase.

Depolymerization can be effected in a batch, semi-continuous, or continuous process. A batch process means that the reaction system is substantially closed so that reactants and products cannot leave the reaction zone as reaction progresses. A semi-continuous process means that the polyamide is placed in the reaction system but the ammonia or amine are passed through the reaction zone and volatiles from the reaction are collected away from the reaction zone. Continuous process means that a steady state, or a substantially steady state is achieved, which means that there is a continuous feed of starting materials and reaction products. A continuous process is generally preferred.

The nitrogen-containing compounds can be separated from the monomeric components using known techniques exemplified by steam and vacuum distillation. Distillation can take place in one or more steps. If desired, these nitrogen-containing compounds, as well as other products of the reaction, can be returned to the depolymerization reactor for reuse. The monomeric components and their precursors can be subsequently purified by means of, for example, steam or vacuum distillation, recrystallization, and other customary purification techniques.

The present process can be advantageously applied to the processing of polyamide, products made of or containing polyamide, and in particular, industrial carpet waste and post-consumer carpet waste. For application of the process to carpet waste, the carpet is preferably first subjected to mechanical size reduction by, for example, grinding, chopping, cutting, or a combination thereof. The non-polyamide components, which may be the larger portion, can be separated from the polyamide components in one or more separation steps. The larger, non-polyamide part can be, for example, latex, jute, polypropylene, or mixtures thereof. The latex may be filled with, for example, $CaCO_3$.

However, the carpet shreds also can be directly fed to the depolymerization reactor. In general, the present process yields good results at polyamide levels in the carpet or heterogeneous starting materials as low as 1 wt. %. The amount of polyamide in the carpet or heterogeneous starting materials may vary in a continuous process.

A process for the depolymerization of polyamides is disclosed in the Belgium patent application Serial No. 9500347, filed Apr. 14, 1995, the complete disclosure of which is hereby incorporated by reference.

EXAMPLES

Example I 40.0 g of nylon 6 was introduced into a 2-liter CrNi steel reactor under a small nitrogen flow at 290° C. After about 2 minutes, the supply of ammonia gas was started (285 NL/h). This flow rate provided an amount of ammonia in the ranges previously indicated herein. This was done via a spiral line discharging into a feed opening at the center of the reactor bottom. Both the gas feed line and the reactor were heated by means of a salt bath at a temperature of 350° C. Depolymerization was carried out at a temperature of 330° C. and pressure of 1 atm. Ammonia was continuously supplied to the reactor and continuously exited the reactor.

A misty, aerosol-like off-gas was formed, which was continuously removed from the reactor. At colder spots, condensate separated from the aerosol and deposited on the walls of the discharge tubing. The aerosol, condensate, and separated deposit were all continuously collected in water. Thus, after 2 hours a total amount of 8.3 g of product had been recovered in water. Analysis of this 8.3 g of product indicated that this product consisted of: 83.3 wt. % caprolactam, 12.9 wt. % aminocaproic acid, 2.0% wt. % aminocaproamide, and 4.3 wt. % aminocapronitrile. The residue in the reactor had a white color, which means that tar formation or degradation had not occurred and implies that the residue can be again subjected to a depolymerization reaction.

The selectivity (sel.) towards nylon 6 monomeric components was 97% as determined by the following equation:

$$\text{sel.} = \frac{\text{mmol monomeric components}}{\text{mmole monomeric components} + \text{mmole by-products}} \times 100\%$$

After purification, caprolactam and aminocaproic acid were directly available for reuse. In contrast, aminocaproamide and aminocapronitrile were converted to caprolactam and aminocaproic acid by means of hydrolysis and cyclization reactions.

Example II

Into a stirred 2-liter double-walled CrNi steel reactor, 45 g of nylon 6 was introduced as well as 4.5 g of ammonium dihydrogen phosphate, while a small nitrogen flow was being passed through at 310° C. After about 2 minutes, the supply of ammonia gas was started (194 Nl/h) via a jacketed feed line discharging into a feed opening at the center of the reactor bottom. Both the feed line and the reactor were heated by means of oil at a temperature of 330° C. The depolymerization was carried out at a temperature of 315° C. and a pressure of 1 atmosphere.

A misty, aerosol-like off-gas was formed which was immediately removed from the reactor. The double-walled cover of the reactor (oil-heated) as well as the gas discharge line were heated at a temperature of 250° C. The resulting gas flow was condensed with the help of a spiral condenser heated at 90° C. Thus, a total of 38.4 g of product was recovered after 1 hour consisting of: 83.4 wt. % caprolactam, <0.1 wt. % aminocaproic acid, 0.8 wt. % aminocaproamide, 11.8 wt. % aminocapronitrile.

The residue in the reactor was clear and of a light brown color, which meant only little tar formation and/or degradation had occurred. The selectivity was 87%.

Comparative Example A 40 g of nylon 6 was depolymerized in a 2-liter autoclave in the presence of 1.3 g of diammonium hydrogen phosphate. Liquid ammonia was fed at a rate of 11 ml/min into the autoclave at a temperature of 320° C. A pressure valve was used to control the autoclave pressure at 68 atm. The pressure was 68 atm. The volatile reaction products left the autoclave via the off-gas. The off-gas was continuously collected in water. The monomers yield was as follows: 37 wt. % caprolactam, 0 wt. % aminocaproic acid, 50 wt. % aminocaproamide, and 1 wt. % aminocapronitrile. The selectivity towards nylon 6 monomeric components was only 45%.

Example III

Part A

Example II was repeated except that 1.5 g ammonium dihydrogen phosphate was used. After 1 hour, a total amount of 30.5 g of product had been recovered in 5 fractions. The fractions were collected after 10, 20, 30, 40, and 60 minutes. Analysis of this 30.5 g indicated that the product consisted of: 79.6 wt. % caprolactam, 0.5 wt. % aminocaproic acid, 0.4 wt. % aminocaproamide, and 15.0 wt. % aminocapronitrile. The selectivity was 84%. The residue was light brown.

In Table 1 the weight and the composition of each fraction is given.

TABLE 1

| Fraction (no) | Weight (g) | Caprolactam (mmole) | Aminocaproamide (mmole) | Aminocaproic acid (mmole) | Aminocapronitrile (mmole) |
|---|---|---|---|---|---|
| 1 | 12.0 | 91.6 | 0.2 | 0.3 | 7.0 |
| 2 | 8.5 | 61.5 | 0.2 | 0.3 | 11.8 |
| 3 | 5.6 | 38.0 | 0.2 | 0.3 | 10.0 |
| 4 | 2.7 | 16.3 | 0.2 | 0.2 | 6.1 |
| 5 | 1.7 | 7.6 | 0.2 | 0.1 | 5.9 |

Part B

Immediately after the Part A depolymerization, depolymerization was repeated, without the residue having been removed from the reactor. Again, 45 g of nylon 6 was introduced into the reactor while a small nitrogen flow was passed through at 310° C., but no fresh additional ammonium dihydrogen phosphate was added.

After 50 minutes, 39.1 g of product was recovered in four fractions with fractions being collected after 10, 20, 30, and 50 minutes. Analysis of this 39.1 g indicated that it consisted of: 76.7 wt. % caprolactam, 0.4 wt. % aminocaproic acid, 0.4 wt. % aminocaproamide, and 15.0 wt. % aminocapronitrile. The selectivity was 84%.

In Table 2 the weight and composition of each fraction is given.

TABLE 2

| Fraction (no) | Weight (g) | Caprolactam (mmole) | Aminocaproamide (mmole) | Aminocaproic acid (mmole) | Aminocapronitrile (mmole) |
| --- | --- | --- | --- | --- | --- |
| 1 | 15.4 | 114.8 | 0.4 | 0.4 | 12.4 |
| 2 | 10.6 | 75.4 | 0.3 | 0.3 | 15.5 |
| 3 | 6.9 | 44.6 | 0.2 | 0.2 | 12.8 |
| 4 | 6.2 | 34.6 | 0.3 | 0.3 | 12.5 |

The results of part A and part B indicate that both the production of the monomers and the selectivity towards the monomers do not differ significantly. Therefore, the catalyst can be recycled. This becomes clear from the selectivity results of part A and part B of this Example.

In addition, both Tables 1 and 2 illustrate that the selectivity and velocity of the depolymerization reaction toward nylon 6 monomeric components (caprolactam and aminocaproic acid) are remarkably better in the first fraction compared with the last fraction. This implies that a continuous depolymerization process can significantly improve the overall selectivity towards nylon 6 monomeric components compared to a batch process.

Example IV

This example was carried out as described in Example II. Instead of ammonia, aminopropane (132 g/h) was used as nitrogen-containing compound. The aminopropane was dosed by evaporating liquid aminopropane in a jacketed feed line discharging into the feed opening at the bottom of the reactor.

After 4 hours, 397.4 g of product including aminopropane was recovered, consisting of: 1.6 wt. % caprolactam, <0.1 wt. % aminocaproic acid, <0.1 wt. % aminocaproamide, and <0.1 wt. % aminocapronitrile. The residue in the reaction had a white color. The selectivity was >95%.

From this example, it can be concluded that with aminopropane high selectivities can be obtained.

Example V

This example was carried out as described in Example II, except that instead of ammonia, 132 g/h of aminopropane was used. Aminopropane dosing took place as described in Example IV.

After 2 hours, 207.7 g of product had been recovered, including aminopropane, in 2 fractions, these fractions being collected at the end of each hour. The 207.7 g consisted of: 15.1 wt. % caprolactam, <0.1 wt. % aminocaproic acid, <0.1 wt. % aminocaproamide, and 0.5 wt. % aminocapronitrile.

The residue in the reactor was clear and of a light brown color, and only little formation of tar and/or degradation had occurred. The selectivity was 96%.

In Table 3 the weight and composition of each fraction is given.

TABLE 3

| Fraction (no) | Weight (g) | Caprolactam (mmole) | Aminocaproamide (mmole) | Aminocaproic acid (mmole) | Aminocapronitrile (mmole) |
| --- | --- | --- | --- | --- | --- |
| 1 | 120.2 | 271.2 | <1 | 1.2 | 7.3 |
| 2 | 87.5 | 6.0 | <1 | <1 | 2.6 |

It becomes clear from Table 3 that over 95% of the nylon 6 monomeric components were produced in the first hour at a selectively higher than 97%. Again, as in Example III, it can be concluded that continuous operation of the depolymerization process according to the present invention results in very high or high selectivity.

While the invention has been described and with reference to specific embodiments thereof, it will be apparent to those of ordinary skill in the art that various changes and modifications can be made therein without departing from the spirit and scope thereof.

What is claimed is:

1. A process comprising the step of heating at least one polyamide comprising nylon 6 in the presence of ammonia, an amine, or a mixture thereof at a temperature between about 200° C. and about 400° C. and at a pressure between about 0.5 atm and about 5 atm to effect at least partial depolymerization of said polyamide and yield monomeric components of said polyamide.

2. A process according to claim 1, wherein said pressure is between about 0.9 and about 3 atm.

3. A process according to claim 1, wherein said amine is at least one of the following: (i) an amine containing a $C_1$–$C_{20}$ aliphatic or cycloaliphatic group, (ii) a diamine containing a $C_1$–$C_{20}$ aliphatic or cycloaliphatic group, (iii) a polyamine containing a $C_1$–$C_{20}$ aliphatic or cycloaliphatic group, (iv) a $C_6$–$C_{20}$ aromatic amine, (v) a $C_6$–$C_{20}$ aromatic diamine, or (vi) a $C_6$–$C_{20}$ aromatic polyamine.

4. A process according to claim 3, wherein said amine has a boiling point lower than the caprolactam boiling point.

5. A process according to claim 3, wherein said amine is aminopropane, diaminoethane, diaminobutane, diaminohexane, or a mixture thereof.

6. A process according to claim 1, wherein said ammonia, amine, or mixture thereof is present in an amount of at least about 1 mole per mole of amide group in said polyamide.

7. A process according to claim 1, wherein an accelerator is present during said heating step which comprises at least one Lewis acid, Brønsted acid, polyamide oligomer, or a metallic component capable of complexing with said ammonia or amine.

8. A process according to claim 7, wherein said accelerator comprises at least one Lewis acid, Brønsted acid, or polyamide oligomer present in an amount between about 0.1 wt. % and about 20 wt. % relative to said nitrogen-containing compound.

9. A process according to claim 7, wherein said accelerator comprises at least one metallic component present in an amount between about 0.1 and about 10 wt. % relative to said nitrogen-containing compound.

10. A process according to claim 1, wherein said heating step is carried out in the presence of water in amounts of at most about 50 wt. % water relative to said polyamide.

11. A process according to claim 1, further comprising the steps of removing and separating said ammonia, amine, or mixture thereof after said heating step, and performing an additional polyamide heating step to effect polyamide depolymerization in the presence of at least some of said separated ammonia or amine.

12. A process according to claim 1, wherein said polyamide is part of a polyamide-containing carpet waste.

13. A process according to claim 1, wherein said process is effected semi-continuously or continuously.

14. A process according to claim 13, wherein said process is effected continuously.

15. A process according to claim 1, wherein said amine is aminopropane.

16. A process according to claim 1, wherein said monomeric components comprise caprolactam, aminocaproic acid, or a mixture thereof.

17. A process according to claim 7, wherein said accelerator comprises a boric acid, boric acid salt, phosphoric acid, phosphoric acid salt, or a mixture thereof.

18. A process comprising the step of heating at least one polyamide comprising nylon 6 in the presence of ammonia, an amine, or a mixture thereof at a temperature between about 200° C. and about 400° C. and at a pressure between 0.5 and 5 atm to effect at least partial depolymerization of said polyamide to yield monomeric components of said polyamide at selectivity greater than about 60%.

19. A process according to claim 18, wherein said process is a semicontinuous or continuous process.

20. A process comprising the step of continuously depolymerizing at least one polyamide comprising nylon 6 in a reaction zone in the presence of ammonia, an amine, or a mixture thereof under substantially steady-state conditions to generate (i) at least some partially depolymerized polyamide in said reaction zone, and (ii) polyamide monomeric components in said reaction zone, wherein said polyamide and said ammonia, amine, or mixture thereof are continuously fed to said reaction zone, and said polyamide monomeric components are substantially and continuously removed from said reaction zone to achieve said substantial steady-state, the selectivity for said monomeric components being greater than about 60%.

* * * * *